US005741640A

United States Patent [19]
Fuller

[11] Patent Number: 5,741,640
[45] Date of Patent: Apr. 21, 1998

[54] DNA CYCLE SEQUENCING

[75] Inventor: Carl W. Fuller, Cleveland Heights, Ohio

[73] Assignee: Amersham Life Science, Inc., Cleveland, Ohio

[21] Appl. No.: 443,468

[22] Filed: May 18, 1995

Related U.S. Application Data

[60] Division of Ser. No. 227,702, Apr. 14, 1994, and a continuation-in-part of Ser. No. 767,137, Sep. 27, 1991.

[51] Int. Cl.⁶ .................. C12Q 1/68; C12Q 1/70; C12P 19/34; A61K 38/54
[52] U.S. Cl. .................. 435/6; 435/91.1; 435/91.2; 435/5; 424/94.1; 536/24.3; 536/24.33; 536/24.32
[58] Field of Search .................. 435/91.2, 91.1, 435/6, 5; 424/94.1; 536/24.3–24.33

[56] References Cited

U.S. PATENT DOCUMENTS

| | | | |
|---|---|---|---|
| 4,795,699 | 1/1989 | Tabor et al. | 435/5 |
| 4,851,331 | 7/1989 | Vary et al. | 435/6 |
| 4,965,188 | 10/1990 | Mullis et al. | 435/6 |
| 5,075,216 | 12/1991 | Innis et al. | 435/6 |

OTHER PUBLICATIONS

Borowi–Borowski et al. Biochemistry 29:2992–2999, 1990.
Kim et al. Korean Biochem. J. 26 (6) 579–82, Abstract cited (of interest), 1993.
Donovan et al., "Detection of the product of the polymerase chain reaction using alkaline phosphatase," *J. Cell. Biochem.* Suppl 13E, 282 (1989) (Abstact).
Higuichi and Ochman, *Nucleic Acids Research* 17:5865 (1989).
Innis et al., *Proc. Natl. Acad. Sci. USA* 85:9436–9440 (1988).
Khrishnan et al., *Nucleic Acids Research* 19:1153.
Maniatis et al., *Molecular Cloning: A Laboratory Manual*, Cold Spring Harbor, New York, New York, pp. 134–135 (1982).
Mead et al., Abstract No. 99, Human Genome II, Oct. 22, 1990.
Murray, *Nucleic Acids Research* 17:889 (1989).
Smith et al., *BioTechniques* 9:52 (1990).
Spurgeon and Burke, Abstract 125, Human Genome II, Oct. 22, 1990.
Straus and Zagursky, *BioTechniques* 10:376 (1991).

*Primary Examiner*—W. Gary Jones
*Assistant Examiner*—Dianne Rees
*Attorney, Agent, or Firm*—Lyon & Lyon

[57] ABSTRACT

Method for sequencing DNA which includes the following steps: providing a polynucleotide primer complementary to a region of the DNA to be sequenced providing the DNA to be sequenced, and contacting that primer and DNA together in the presence of a DNA polymerase and between 1 and 3 dNTPs, at least one of the dNTPs being labeled. The primer and DNA are contacted under conditions which allow extension of the primer by addition of one or more of the dNTPs to the primer to form an extended primer. The primer and DNA are then dissociated, generally by heating, and the contacting and dissociating steps repeated a plurality of times (usually 10–200 times). Finally, the extended primer is contacted with the DNA in the presence of a DNA polymerase (which is generally the same polymerase as used in the initial labeling step) all four dNTPs and a chain terminating agent.

18 Claims, 7 Drawing Sheets

```
PRIMER (UNIVERSAL -40, PRESENT IN EXCESS)
    GTTTTCCCAGTCACGAC
    CCCAAAAGGGTCAGTGCTGCAACATTTTGCTGCCGG
TEMPLATE (M13mp 18)
                           │ Δ Taq DNA POLYMERASE
                           │ dGTP, dTTP, [α-³⁵S]dATP
                           │ 50-100 CYCLES
                           │ LABELING STEP
                           ▼
    GTTTTCCCAGTCACGAC GTTGTAAAA
    CCCAAAAGGGTCAGTGCTGCAACATTTTGCTGCCGG
                  +
    GTTTTCCCAGTCACGAC GTTGTAAAA
    (50-100 COPIES PER TEMPLATE MOLECULE)
                           │ dNTPs, ddNTP
                           │ 4 REACTIONS
                           │ 100-200 CYCLES
                           │ TERMINATION STEP
                           ▼
                    DNA SEQUENCE
```

PRIMER (UNIVERSAL -40, PRESENT IN EXCESS)
  GTTTTCCCAGTCACGAC
    CCCAAAAGGGTCAGTGCTGCAACATTTTGCTGCCGG
TEMPLATE (M13mp 18)

⏐ Δ Taq DNA POLYMERASE
⏐ dGTP, dTTP, [α-$^{35}$S]dATP
⏐ 50-100 CYCLES
⏐ LABELING STEP
▼

GTTTTCCCAGTCACGAC GTTGTAAAA
    CCCAAAAGGGTCAGTGCTGCAACATTTTGCTGCCGG

+

GTTTTCCCAGTCACGAC GTTGTAAAA
(50-100 COPIES PER TEMPLATE MOLECULE)

⏐ dNTPs, ddNTP
⏐ 4 REACTIONS
⏐ 100-200 CYCLES
⏐ TERMINATION STEP
▼
  DNA SEQUENCE

FIG. 8a. A. ΔTaq Fluorescein-dUTP Cycle Sequencing Raw Data

FIG. 8b. B. ΔTaq Fluorescein-dUTP Cycle Sequencing Normalized Data
A A G T A A A G C C T G G G G T G C C T A A T G A G T G A G C T A A C T C A C A

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

GGTTATCGAA ATCAGCCACA GCGCC    25

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

TCCCGTT    7

( 2 ) INFORMATION FOR SEQ ID NO:3:

( i ) SEQUENCE CHARACTERISTICS:

-continued (A) LENGTH: 17 base pairs
(B) TYPE: nucleic acid
(C) STRANDEDNESS: single
(D) TOPOLOGY: linear (xi) SEQUENCE DESCRIPTION: SEQ ID NO:3:

GTTTTCCAG TCACGAC    17

(2) INFORMATION FOR SEQ ID NO:4:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:4:

TTCACACAGG AAACAG    16

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:5:

CAAAAGGGTC AGTGCTGCAA CATTTGCTG    30

(2) INFORMATION FOR SEQ ID NO:6:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:6:

GTTTTCCAG TCACGACGUU GUAAAA    26

DNA CYCLE SEQUENCING

This is a division of application Ser. No. 08/227,702, filed Apr. 14, 1994 hereby incorporated by reference in its totality (including drawings) which is a continuation-in-part of U.S. application Ser. No. 07/767,137, filed Sep. 27, 1991, which is hereby incorporated by reference herein.

BACKGROUND OF THE INVENTION

This invention relates to methods for DNA sequencing in which a labeled nucleotide is incorporated into an extending DNA molecule during a chain termination sequencing method.

The sequence of nucleotide bases in a DNA molecule can be determined in a variety of ways. The chain termination method generally involves synthesizing DNA complementary to the template strand to be sequenced by extending a primer able to hybridize to a portion of that template strand with a DNA polymerase. During the synthesis reaction, deoxynucleoside triphosphates (dNTPs) are incorporated to form a DNA fragment until a chain terminating agent, for example, a dideoxynucleotide triphosphate (ddNTP) is incorporated. Incorporation of a ddNTP prevents further DNA synthesis (a process called chain termination). The size of each DNA fragment synthesized in this procedure is then determined by gel electrophoresis and this information used to determine the sequence of nucleotides in the original template DNA. For example, Tabor and Richardson, U.S. Pat. No. 4,795,699, describe a two step sequencing method in which an unlabeled primer is labeled in a labeling step, and then extended in the presence of excess dNTPs and a ddNTP in a chain termination step. In the labeling step a low concentration of dNTPs is provided (one being labeled) to allow a small amount of primer extension.

In the dideoxy sequencing method, the primer may be labeled, for example, with $^{32}P$, by a process using a polynucleotide kinase. Such labeling allows detection of extended primers after gel electrophoresis by autoradiography of the resulting gel. Alternatively, a labeled dNTP may be incorporated during the process of DNA synthesis, and the presence of such labeled dNTPs detected by autoradiography or other means. To this end, the dNTP may be labeled either radioactively with $^{32}P$ or $^{35}S$. In another procedure, the primer can be labeled with one or more fluorescent moieties for detection by fluorescence. In yet another procedure, the ddNTP may be labeled, for example, with a fluorescent marker.

Examples of these procedures are provided in the following publications, none of which are admitted to be prior art to the present application:

Murray, 17 *Nucleic Acid Research* 8889, 1989 describes use of a $^{32}P$-labeled primer. The primer was labeled by use of a polynucleotide kinase and gamma-$^{32}P$ ATP.

Higuchi and Ochman, 17 *Nucleic Acid Research* 5865, 1989, describe use of a kinase-labeled primer for sequencing DNA fragments produced by a polymerase chain reaction (PCR). PCR is a method for amplifying a desired nucleic acid by use of two primers which are extended by a DNA polymerase to produce a pair of DNA fragments complementary to the desired nucleic acid. These fragments then hybridize to provide the desired DNA. This process is repeated 15–30 times. If a thermostable DNA polymerase is used, the process is best cycled by maintaining the temperature of the reaction alternatively at a temperature suitable for primer extension (70°–75° C.), then at a temperature suitable for denaturation (90°–100° C.) to separate the DNA fragments and provide a template for the next cycle, and then at a temperature suitable for annealing (42°–55° C.) to bind primers to the template.

Straus and Zagursky, 10 *BioTechniques* 376, 1991, describe use of α-$^{32}P$ dATP in a sequencing reaction.

Smith et al., 9 *BioTechniques* 52, 1990, and Adams-Blakesley, 13 *Focus* 56, 1991, describe sequencing of PCR products using a labeled primer.

Khrishnan et al., 19 *Nucleic Acid Research* 1153, 1991, describe use of a labeled primer for sequencing lambda DNA. The process of chain termination is repeated (or cycled) several times to allow production of a large number of products. This cycling is similar to a PCR since the reaction is allowed to proceed at 42°–55° C., then stopped at 95° C., and started again at 42°–55° C. (the process is called thermal cycle sequencing). No new reagent need be added once the process is started. The cycling ensures that a large proportion of the labeled primer is extended in the chain termination steps.

Spurgeon and Burke, *Abstract* 125, Human Genome II, Oct. 22, 1990, describe use of a modified Taq DNA polymerase for thermal cycle sequencing in which an end-labeled primer, or an unlabeled primer is used. Fluorescent labeled ddNTPs and radioactive labeling techniques were also used.

Mead et al., Abstract No. 99, Human Genome II, Oct. 22, 1990, describe sequencing of lambda DNA in a polymerase chain-based reaction, using radioisotopes and fluorescent labels.

SUMMARY OF THE INVENTION

This invention features a novel DNA sequencing method in which an unlabeled primer is extended in a labeling reaction performed in a cyclical manner. Such a method is advantageous over the prior use of $^{32}P$ end-labeled primers (prepared using polynucleotide kinase and γ-$^{32}P$ ATP), since no additional reagents (e.g., polynucleotide kinase, and γ-$^{32}P$ ATP) are required over the usual sequencing reagents, the process of preparing labeled primer is not required, and, since the apparatus used in the method is identical to that which is used for thermal cycle sequencing, the two methods can be conveniently used together. This procedure allows the use of labels not otherwise usable with polynucleotide kinase, such as α-$^{35}S$ dNTPs, fluorescent nucleotides, and nucleotides labeled with other useful moieties, such as biotin.

The critical feature of the present invention is the use of at least one labeled nucleotide in a cycled labeling step. This is generally followed by a cycled termination step. The repeated cycling of primed DNA synthesis results in production of many more newly synthesized molecules of DNA than molecules of template DNA used for sequencing. Thus, while sequencing using customary amounts of template (0.5–1.0 pmol) is possible when only a single round of replicative synthesis is performed, sequencing using less template DNA (e.g., 0.05 pmol) without a cycling step is difficult. Repeated cycling of the labeling step using limited amounts of template increases the amount of product to a level sufficient for normal detection procedures, such as autoradiography with overnight exposure.

In the method, at most three of the four required dNTPs for a sequencing reaction are present in the labeling step, with one or more of them being labeled. This effectively labels the primer and limits extension to a known length (i.e., to a length where the missing dNTP is required for further synthesis). In the method, the reaction is cycled between a temperature suitable for chain extension, and one suitable for denaturation of the extended primer and template molecules, generally 10 to 100 times over a period of one and one-half to six hours. After this labeling step, the reaction is generally divided into four portions and an appropriate chain terminating mix, including the missing dNTP, is supplied to the reaction mixture and cycled between 10 and 200 times at appropriate temperatures for primer extension and denaturing. No additional DNA polymerase is required in this step, and the reaction can be completed in 1.5 to 16 hours.

The method of this invention allows sequencing of as little as 0.01 micrograms (0.005 picomoles) of M13 DNA with an 18 to 36 hour exposure for radioactively-labeled ($^{35}S$) material. With double-stranded plasmids, sequence information can be obtained from as little as 0.03 micrograms (0.015 pmol), without prior denaturation of the plasmid DNA with alkali. In addition, reliable sequence data can be obtained directly from a single M13 plaque, without further growth of the phage, by simply picking the plaque into a reaction vessel and adding the appropriate reagents. In addition, sequences can be obtained from single colonies of bacteria containing plasmids having the f1 replication origin (e.g., pTZ18R or pUC118) with a helper phage (M13 KO7), or even for plasmids without helper phage.

Because the invention allows sequencing of small quantities of template, the need to grow clones and purify DNA from them is unnecessary, and the chance of adding impurities into the sequencing reaction along with the template DNA is thus reduced. In addition, because the DNA is effectively end-labeled by this procedure, there is little systematic variation in band intensity and no tendency for sequences to fade near the bottom of an autoradiogram of a sequencing gel.

Furthermore, the invention allows sequencing of plasmid and other double-stranded DNA templates without prior denaturation using alkali. These denaturation procedures are tedious, requiring an hour or more of skilled manipulation for denaturation and subsequent precipitation. Thus, the invention allows sequencing of DNA using existing apparatus with little modification to the procedure necessary to perform the claimed DNA sequencing reaction.

Thus, in a first aspect, the invention features a method for sequencing DNA which includes the following steps: providing a polynucleotide primer complementary to a region of the DNA, providing the DNA to be sequenced, and contacting that primer and DNA together in the presence of a DNA polymerase and between 1 and 3 dNTPs, at least one of the dNTPs being labeled. The primer and DNA are contacted under conditions which allow extension of the primer by addition of one or more of the dNTPs to the 3'-end of the primer to form an extended primer. The primer and DNA are then dissociated, or separated, generally by heating, and the contacting and separating steps repeated a plurality of times (usually 10–200 times). Finally, the extended primer is contacted with the DNA in the presence of a DNA polymerase (which is generally the same polymerase as used in the initial labeling step), all four dNTPs and a chain terminating agent.

In preferred embodiments, the DNA polymerase is Taq DNA polymerase (e.g., a form of Taq polymerase lacking a 5'-3' exonuclease activity), a low exonuclease form of T7 DNA polymerase (see Tabor and Richardson, U.S. Pat. No. 4,795,699), Klenow, AMV reverse transcriptase, Bst, Tth or Vent DNA polymerase, or exo-free forms of such polymerases; the dNTP is labeled with $^{35}S$ or a fluorescent, chemiluminescent or other (e.g., are detectable as a ligand by indirect enzyme-linked assay, e.g., biotin) label; and the final contacting step in the presence of a chain terminating agent is followed by a separation step in which the extended primer is separated from the DNA, and those two steps repeated a plurality of times (e.g., between 30 and 200 times) until approximately 0.1–1.0 picomole (preferably 0.5 pmole) of labeled extended primer which is terminated by a dideoxynucleotide at its 3' end is produced.

In other preferred embodiments, the method is used to sequence:

Purified M13 DNA (single stranded, ss),

Purified Plasmid DNA (Double-stranded, ds),

Purified Lambda DNA (ds),

M13 DNA from a plaque or liquid culture (ss),

Plasmid DNA from a colony or liquid culture (ds),

Plasmid-with-f1-ori, preferably, infected with helper phage, from a colony (ss), PCR product, e.g., gel purified (ds), PCR product treated w/ExoI and Alk. Phos. (ds), Asymmetric PCR product treated with Alk. Phos. (ss), Purified Cosmid DNA, and DNA from other sources e.g., yeast or bacterial genomic DNA or other phage DNAs.

Other features and advantages of the invention will be apparent from the following description of the preferred embodiments thereof, and from the claims.

DESCRIPTION OF THE PREFERRED EMBODIMENTS

The drawings will first briefly be described.

There follow examples of methods of the invention. These examples are not limiting in the invention, and those of ordinary skill in the art will recognize that the components used in the reactions may be readily substituted with equivalent reagents known in the art.

Methods

Figure 1:
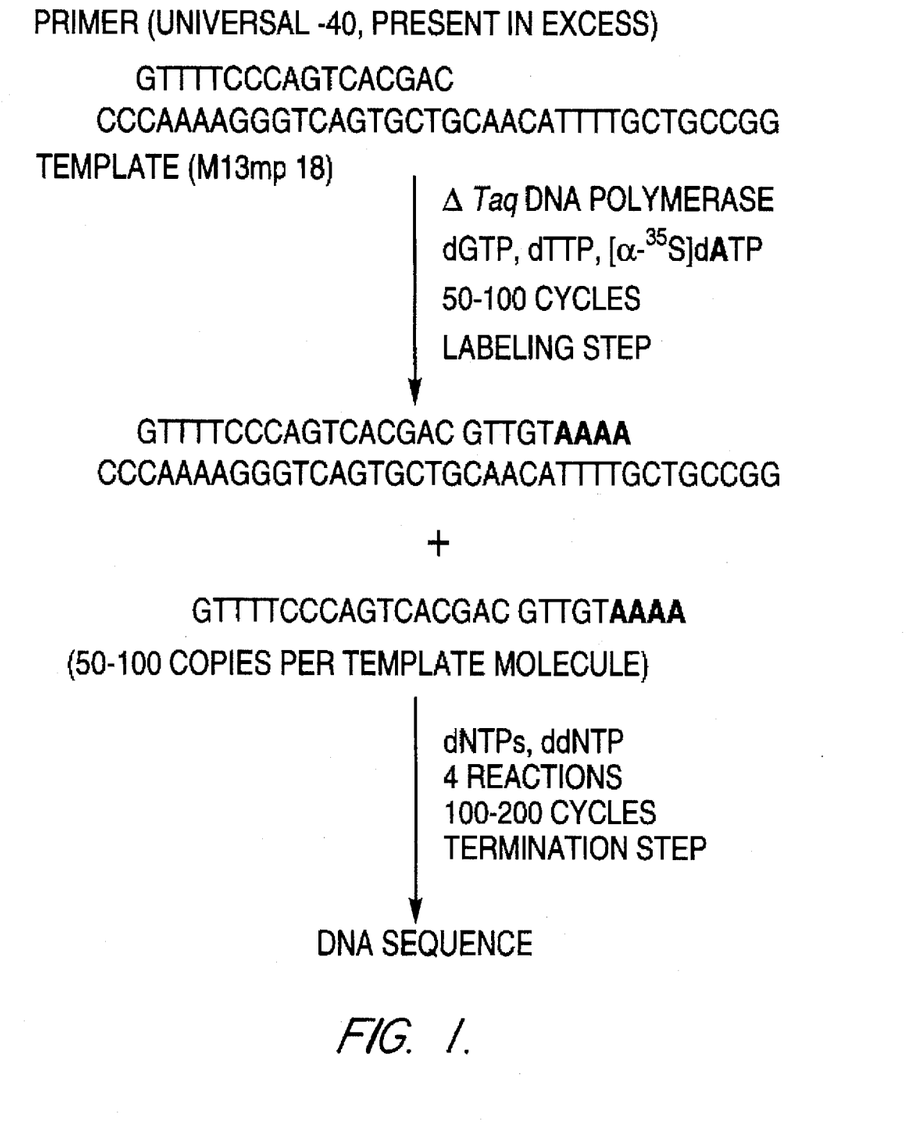
FIG. 1 is a diagrammatic representation of a DNA sequencing procedure of this invention.
Figure 2A:
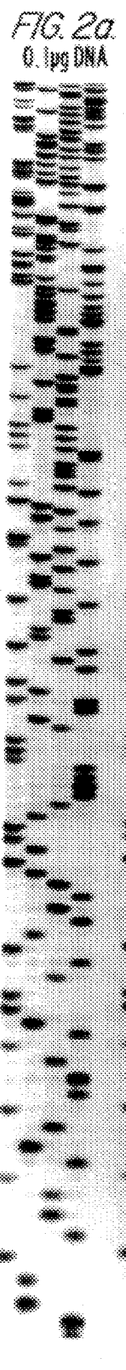
FIG. 2 is a copy of an autoradiogram obtained from a DNA sequencing experiment utilizing M13mp18 DNA using conditions described in Example 1.
Figure 2B:
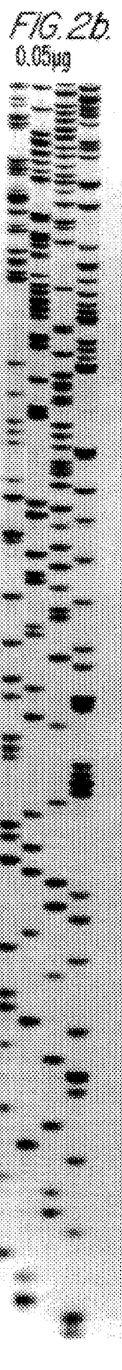
Figure 2C:
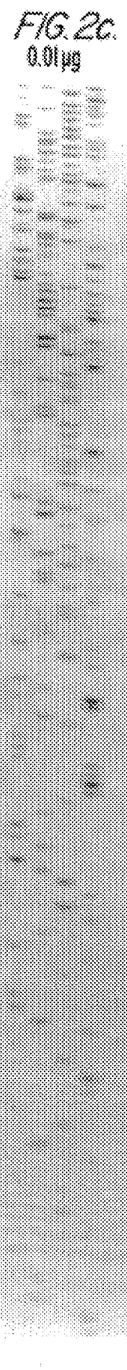
Figure 2D:
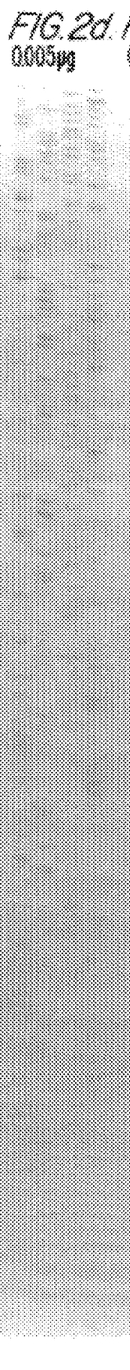
Figure 2E:
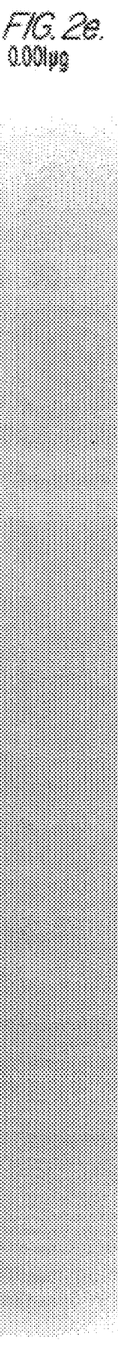
Figure 2F:
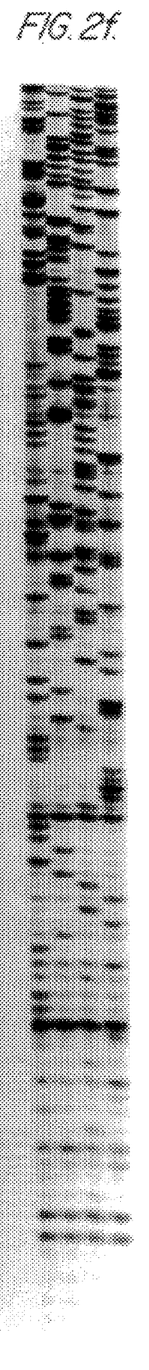
Figure 3A:
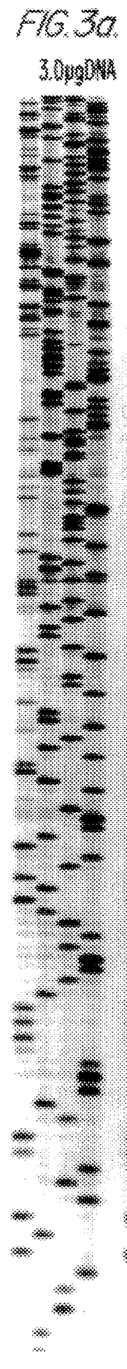
FIG. 3 is a copy of an autoradiogram obtained from a DNA sequencing experiment utilizing plasmid (pUC19) DNA using conditions described in Example 3.
Figure 3B:
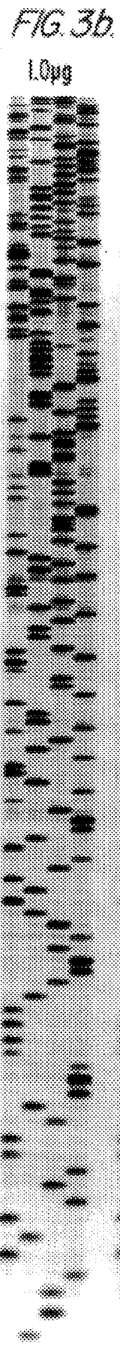
Figure 3C:
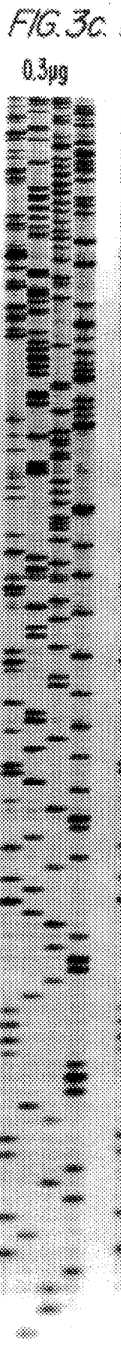
Figure 3D:
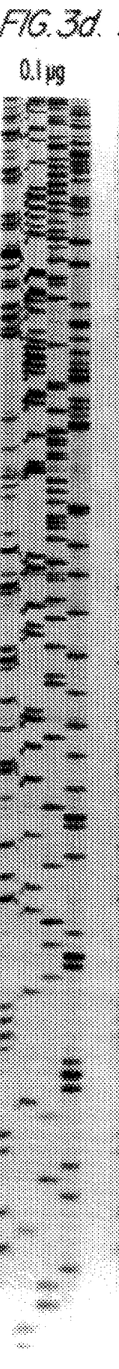
Figure 3E:
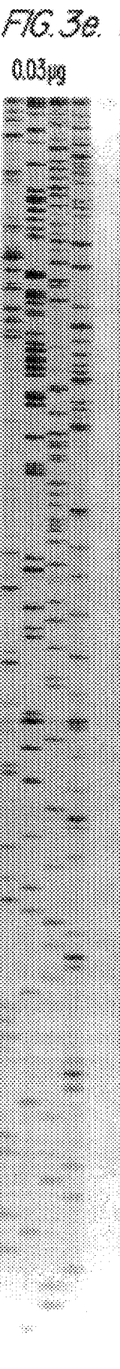
Figure 3F:
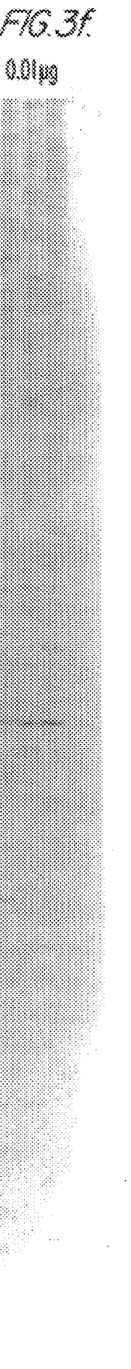

Referring to FIG. 1, the first step in the method is to examine the sequence of the template (usually vector sequence) and choose a combination of primer and labeling nucleotides. The primer is chosen by standard criteria, well known in the art, to prime DNA synthesis near the sequence of interest. The primer is typically a synthetic oligonucleotide 16–25 nucleotide bases in length.

A mixture of three nucleotides (of the possible four: dATP, dCTP, dGTP and dTTP) is chosen as follows: The first place where dAMP will be incorporated downstream from the 3' terminus of the primer is located. Similarly, the first sites for incorporation of dGMP, dCMP and dTTP are found. One of these sites will be farther from the primer than all the others. The nucleotide required at this site is omitted during the labeling phase of the protocol (dCTP in FIG. 1). One or more of the remaining three nucleotides must be labeled (e.g., $\alpha$-$^{32}$P, $\alpha$-$^{35}$S or a fluorescent molecule). A combination is chosen so that at least 2 labeled nucleotides will be incorporated prior to termination at the point where the missing nucleotide terminates extension. In FIG. 1, there are four dAMP nucleotides incorporated prior to the first site where dCMP would be required. Thus, a labeled dATP is a good choice in this example.

A suitable combination of primer and nucleotide mix can usually be found without difficulty, however, vectors can be specifically engineered for optimal labeling of sequences. If necessary the choice of which dNTP to leave out of the labeling mix can be determined empirically by running test labelings.

EXAMPLE 1

Sequencing with Purified M13 DNA or Purified Plasmid DNA

The following components were added to a microcentrifuge vial (0.4 ml) which was inserted into a thermocycler machine (e.g., Perkin-Elmer DNA Thermal Cycler): 0.005 pmol or more M13 DNA (e.g., M13mp18, 0.01 µg), or 0.03 µg double-stranded plasmid DNA (e.g., pUC19); 2 µl ΔTAQ Reaction Buffer (United States Biochemical Corporation, Cleveland, Ohio, 260 mM Tris-HCl, pH 9.5 65 mM MgCl$_2$); 1 µl 3.0 µM dGTP; 1 µl 3.0 µM dTTP; 0.5 µl (5 µCi) of [$\alpha$-$^{35}$S]dATP (about 1200 Ci/mmol); 1 µl −40 primer (0.5 µM; 0.5 pmol/µl SEQ. ID. NO. 3: 5'GTTTTCCCAGTCACGAC-3'); 2 µl ΔTAQ DNA polymerase 32 U/µl (from United States Biochemical Corporation, Cleveland, Ohio, in 20 mM Tris (pH 8.5) 100 mM KCl, 0.1 mM EDTA, 1 mM DTT, 0.5% NP-40, 0.5% TWEEN-20 and 50% glycerol, diluted 8 fold in dilution buffer (10 mM Tris-HCl pH8.0, 1 mM 2-mercaptoethanol, 0.5% TWEEN-20, 0.5% NP-40)); and water to a total volume of 17.5 µl.

These components were mixed and overlaid with 10 µl light mineral oil (United States Biochemical Corporation). The vial was placed in the thermocycler and 30–100 cycles (more than 60 cycles is unnecessary) from 45° C. for 1 minute to 70° C. for 0.5 minute performed. (Temperatures can be cycled from 55°–70° C., if desired, or even a constant temperature of about 62° C. maintained (depending on the melting temperature of the primer and template to be sequenced). Such isothermal labeling is possible, but takes as long to complete (about 4–6 hours) as cycled temperatures.) The temperatures may be adjusted if the melting temperature of the primer/template is significantly higher or lower, but these temperatures work well for most primer/templates. A temperature of 95° C. can be used instead of 70° C. with equivalent results. This step can be completed in about 3 minutes per cycle.

Four vials were labeled A, C, G, and T, and filled with 4 µl of the corresponding ΔTAQ termination mix: ddA termination mix (15 µM each dATP, dCTP, dGTP, dTTP, 300 µM ddATP); ddT termination mix (15 µM each dATP, dCTP, dGTP, dTTP, 450 µM ddTTP); ddC termination mix (15 µM each dATP, dCTP, dGTP, dTTP, 225 µM ddCTP); ddG termination mix (15 µM each dATP, dCTP, dGTP, dTTP, 22.5 µM ddGTP) (United States Biochemical Corporation, Cleveland, Ohio). No additional enzyme is added to the termination vials. The enzyme carried in from the prior step is sufficient.

The cycled labeling reaction was divided equally among the four termination vials (4 µl to each termination reaction vial), and overlaid with 10 µl of light mineral oil.

The four vials were placed in the thermocycler and 30–200 cycles (more than 60 cycles is unnecessary) performed from 95° C. for 15 seconds, 55° C. for 30 seconds, and 72° C. for 120 seconds. This step was conveniently completed overnight. Other times and temperatures are also effective.

Six µl of reaction mixture was removed (avoiding oil), 3 µl of Stop Solution (95% Formamide 20 mM EDTA, 0.05% Bromophenol Blue, 0.05% Xylene Cyanol FF) added, and heated briefly to 70°–80° C. immediately prior to loading on a sequencing gel. Autoradiograms required an 18–36 hour exposure using Kodak XAR-5 film.

Referring to FIGS. 2A–F, the indicated amount of purified M13mp18 DNA (0.001–0.1 µg, in lanes E-A respectively) was sequenced using the −40 primer and nucleotides as described above. The labeling step was cycled 30 times (45° C. to 95° C.) and the termination step was cycled 35 times (95° C., 55° C., and 72° C.). The result in lane F is an example where all four dNTPs were present during the cycled labeling step (3 pmol each).

When the above labeling procedure is performed without cycling (using the standard protocol for the TAQuence sequencing kit, United States Biochemical Corporation), 0.1 µg M13mp18 template DNA yields an autoradiogram where bands representing the first 200 bases from the primer are absent. The use of less DNA yields even fainter sequence.

EXAMPLE 2

Direct Sequencing of M13 Plaque

An M13 plaque (M13mp18) was picked from an 18–36 hour-incubated plate using a large opening pipette tip. More phage can be obtained using a tip with the tip cut back to enlarge the opening to about 1.5 mm diameter. A small amount of soft agar adheres to the tip. The soft agar was mixed well (repeated sucking up and pushing out the liquid in the pipette) with 2 82 1 of reaction buffer and 10 µl of water. The tube was capped and heated for 10 minutes at 95°–100° C., and quickly spun to collect any condensation. 12 µl was then quickly (so the agar does not solidify) removed for sequencing. The procedure outlined in Example 1 was then used for sequencing.

Figure 4:
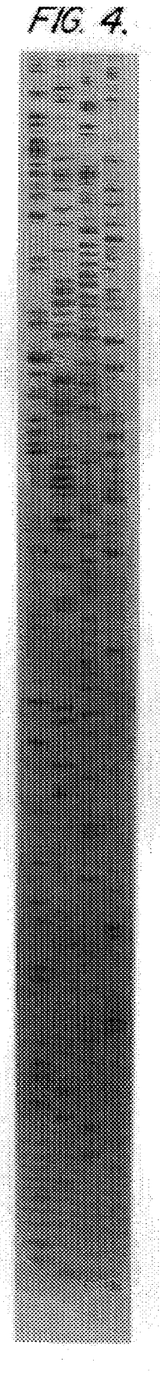
FIG. 4 is a copy of an autoradiogram obtained from a DNA sequencing experiment utilizing a single plaque of M13mp18 picked from a lawn of JM101 under conditions described in Example 2.

Referring to FIG. 4, the sequence of DNA from a single plaque of M13mp18 picked from a lawn of JM101 is shown. The DNA was extracted from the plaque by heating in sequencing buffer at 95°–100° C. for 10 minutes. The DNA was sequenced using the −40 primer and nucleotides as described above. The labeling step was cycled 99 times (45° C. to 95° C.) and the termination step was cycled 198 times (95° C., 55° C., and 72° C.).

EXAMPLE 3

Direct Sequencing of a Colony Containing a Plasmid

A colony containing a cloning vector (e.g., pUC19) is picked from a 36 hour-incubated plate (L broth) using a sterile wire or loop, suspended in 2 µl of reaction buffer and 10 µl of water, and mixed well. The colony was heated at 95°–100° C. for 20 minutes, briefly spun to sediment the debris, and 12 µl of liquid removed for sequencing. The procedure outlined in Example 1 was then used for sequencing.

Referring to FIGS. 3A–F, results of cycled-labeling sequencing of plasmid (pUC19) DNA are shown. The indicated amount of purified pUC19 DNA (0.01–3 µg) was sequenced using the –40 primer and nucleotides as described above. The labeling step was cycled 85 times (45° C. to 95° C.) and the termination step was cycled 198 times (95° C., 55° C. and 72° C.).

EXAMPLE 4

Direct Sequencing of a Colony Containing a Plasmid and Infected with Helper Phage Infection of a cell containing a plasmid with the f1 origin with helper phage results in the production of large amounts of phage-like particles containing one strand of the plasmid DNA. (The strand produced is determined by the orientation of the f1 origin). These are secreted from the cell. Helper phage particles are also produced in lesser quantity (due to an alteration in the helper phage origin) but these do not sequence with the primer used. Thus, when a colony is infected with helper phage more plasmid DNA (but only one strand) is available for sequencing. Plasmid sequencing from a single colony is marginal, probably because it is difficult to obtain sufficient template DNA routinely. Infection with a helper phage produces more template, making sequencing possible.

Host strain JM101 was transformed with a plasmid vector (pTZ18U; Mead et al., 13 *Nucleic Acid Research* 1103, 1985) which contains the replication origin from bacteriophage f1. After incubating the competent cells with the plasmid at 0° C. (45 minutes) and 42° C. (2 minutes), the cells were diluted in L Broth and incubated at 37° C. for 30 minutes. M13 helper phage M13KO7 (Vierra and Messing, 153 *Meth. Enz.* 3, 1987; 10 µl of $10^{10}$ pfu/ml) was added, and incubation continued at 37° C. for 20 minutes. Transformants were then plated on media containing ampicillin and kanamycin. After incubation for 18–36 hours, a single colony was picked.

A colony from an 18–36 hour-incubated plate was picked using a sterile wire or loop, suspended in 2 µl of reaction buffer and 10 µl of water, and mixed well. The mixture was heated at 95°–100° C. for 20 minutes; alternatively, it was heated at 37° C., for 30 minutes centrifuged briefly, and the supernatant incubated at 95°–100° C. for 10 minutes. The supernatant was then briefly spun to sediment the debris, and 12 µl removed for sequencing as above.

Figure 5:
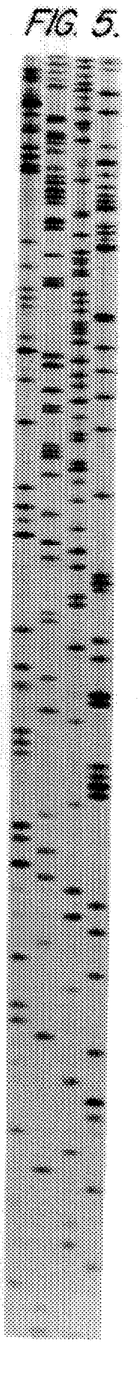
FIG. 5 is a copy of an autoradiogram obtained from a DNA sequencing experiment utilizing DNA from a single colony of JM101 containing pTZ18U infected with M13KO7 using conditions described in Example 4.
Figure 6A:
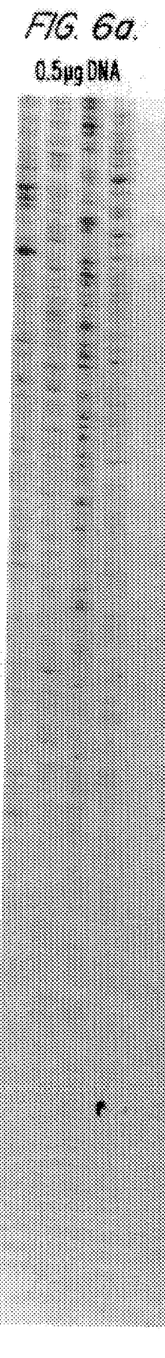
FIG. 6 is a copy of an autoradiogram obtained from a DNA sequencing experiment utilizing bacteriophage lambda DNA using conditions described in Example 5.
Figure 6B:
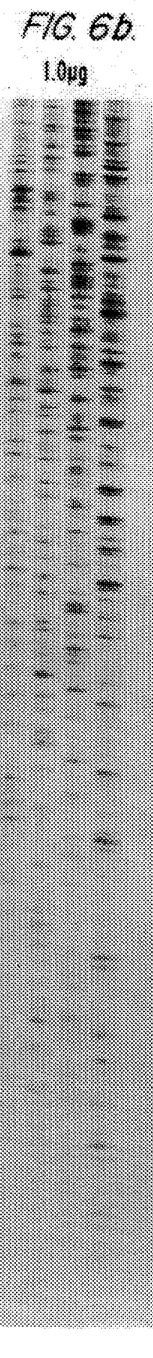
Figure 6C:
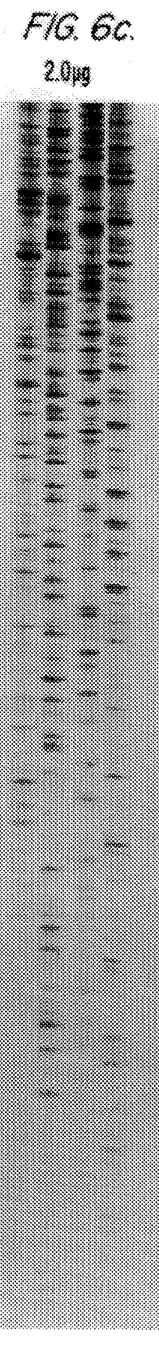
Figure 6D:
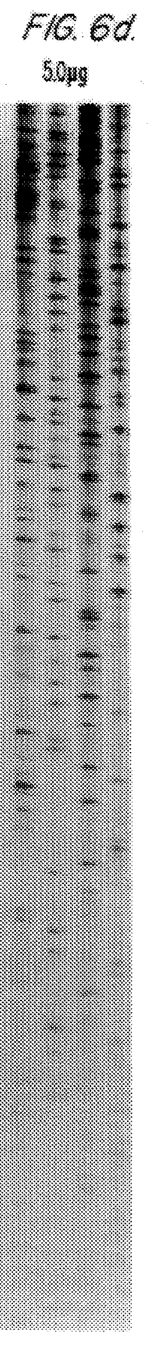

Referring to FIG. 5, the sequence of DNA from a single colony of JM101 containing pTZ18U infected with M13KO7 is shown. The DNA was extracted from the colony by heating in sequencing buffer at 95°–100° C. for 10 minutes. The DNA was sequenced using the –40 primer and nucleotides as described above. The labeling step was cycled 99 times (45° C. to 95° C.) and the termination step was cycled 198 times (95° C., 55° C., and 72° C.).

EXAMPLE 5

Sequencing of DNA Extracted from Bacteriophage Lambda

Purified DNA from bacteriophage lambda (1 µg in 5 µl $H_2O$) was mixed with 1 µl (0.5 pmol) primer (SEQ. ID. NO. 1: 5'-GGTTATCGAAATCAGCCACAGCGCC; corresponding to bases 7630–7606 in bacteriophage lambda), 2 µl ΔTAQ buffer, 1 µl 3 µM dGTP, 1 µl 13 µM dTTP, 0.5 µl $\alpha$-$^{35}$S dCTP (1200 Ci/mmol, 10 µCi/µl) and diluted ΔTAQ DNA polymerase (2 µl 4 U/µl) and 5 µl $H_2O$ for a total volume of 17.5 µl. This mixture was incubated in the DNA Thermal Cycler at 50° C. for 60 seconds, then 90° C. for 30 seconds for 99 cycles. Using this mixture of nucleotides, the primer was extended 7 bases with the sequence (SEQ. ID. NO. 2: TCCCGTT with the C's labeled).

The mixture was then divided into four parts, combining one part with 4 82 1 ddGTP termination mix (15 µM each dATP, dCTP, dGTP, dTTP; 22.5 µM ddGTP), a second with 4 µl ddATP termination mix (15 µM each dATP, dCTP, dGTP, dTTP; 300 ddATP), the third with 4 µl ddTTP termination mix (15 µM each dATP, dCTP, dGTP, dTTP; 450 µM ddTTP) and the fourth with 4 µl ddCTP termination mix (15 µM each dATP, dCTP, dGTP, dTTP; 225 µM ddCTP). The mixtures were overlaid with 10 µl mineral oil and the vials capped. These four vials were then placed in the thermal cycler and subjected to 198 cycles at 95° C., 15 seconds, 55° C., 30 seconds and 72° C., 120 seconds.

Upon completion of the cycles overnight, 6 µl of the aqueous phase was removed from each vial, and 3 µl of stop solution (95% Formamide, 20 mM EDTA, 0.05% Bromophenol Blue, 0.05% Xylene Cyanol FF) added. The mixtures were heated to 75° C. for 2 minutes and applied to the sequencing gel. Sequencing required only 1–2 µg (0.03–0.05 pmol).

Referring to FIGS. 6A–D, the sequence of DNA from bacteriophage lambda DNA using a cycled labeling step protocol is shown. 0.5–5 µg of lambda DNA was used as indicated in the Figures. The autoradiogram shown is the result of a 60 hour exposure.

EXAMPLE 6

Sequencing DNA Produced by a Polymerase Chain Reaction

Upon completion of a polymerase chain reaction, the reaction mixture still contains excess primer, dNTPs and non-specifically amplified single-stranded DNAs. These are typically removed from the desired double-stranded product by precipitation, gel purification or other physical technique. These procedures are usually time-consuming and require manual manipulations for centrifugations or gel electrophoresis. I have discovered that the undesirable single-stranded DNA and primer can be removed by brief incubation with exonuclease I. Similarly, the excess dNTPs (which would interfere with the labeling portion of the sequencing process) can be removed by simultaneous treatment with alkaline phosphatase. Both enzymes can be inactivated by heating briefly. Subsequently, the PCR product can be sequenced using the methods outlined in Example 1.

Specifically, PCR was performed as outlined in the Perkin-Elmer Cetus GENEAMP kit using 200 µM dNTPs, 100 pmol each primer, 1 ng template DNA and buffer in a total volume of 100 µl. Template DNA was pT7L-21 (a clone of a modified Tetrahymena ribozyme in pUC18; Zaug et al., 27 *Biochemistry* 8924–8931, 1988) and the primers were −40 universal sequencing primer (SEQ. ID. NO. 3: 5'-GTTTTCCCAGTCACGAC) and reverse sequencing primer (SEQ. ID. NO. 4: 5'-TTCACACAGGAAACAG). These primers yield a product 518 nucleotides in length. The polymerase chain reaction was performed using 30 cycles of 94° C. for 1 minute, 37° C. for 1 minute and 72° C. for 2 minutes.

An aliquot (10 µl) of the PCR mixture was removed. Exonuclease I (USB Product No. 70013; 1 µl of 10 U/µl) and shrimp alkaline phosphatase (USB Product No. 70092, 1 µl of 1 U/µl) were added. This mixture was incubated at 37° C. for 15 minutes, followed by heat inactivation at 70° C. for 15 minutes. This mixture was diluted to 200–2000 µl with TE buffer (10 mM Tris-HCl, pH7.5, 1 mM EDTA), and 10 µl used for cycle-sequencing according to the method of example 1 using the −40 primer. Control experiments in which the treatments with either exonuclease I or shrimp alkaline phosphatase are omitted failed to provide good sequence data.

Referring to FIGS. 7A–D, the DNA sequence of the product of a polymerase chain reaction using a cycled labeling step protocol is shown. The labeling step was cycled 65 times (45° C. to 70° C.) and the termination step was cycled 198 times (95° C., 55° C. and 72° C.). Aliquots of the PCR reaction mixture were treated with exonuclease I (FIGS. 7A and 7C) and/or shrimp alkaline phosphatase (FIGS. 7B and 7C) as described above, or untreated (FIG. 7D).

Figure 7A:
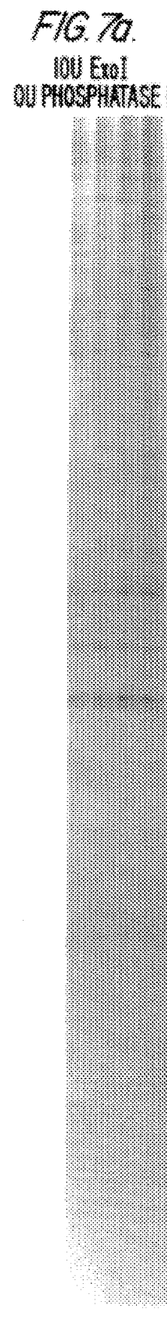
FIG. 7 is a copy of an autoradiogram obtained from a DNA sequencing experiment utilizing the product of a polymerase chain reaction under conditions described in Example 6.
Figure 7B:
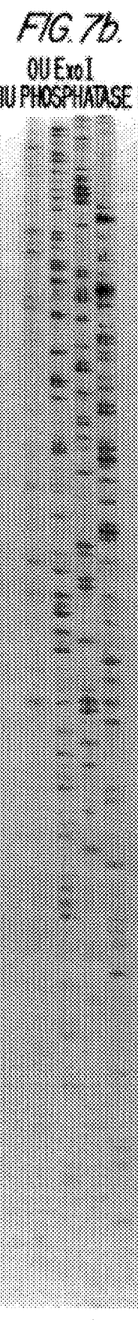
Figure 7C:
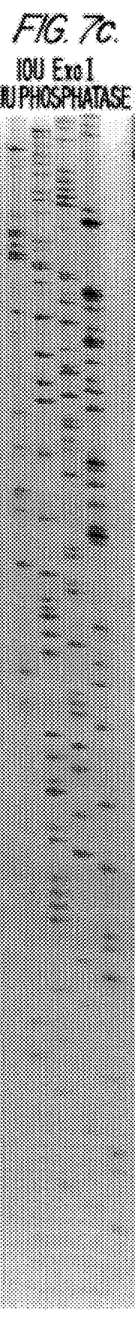
Figure 7D:
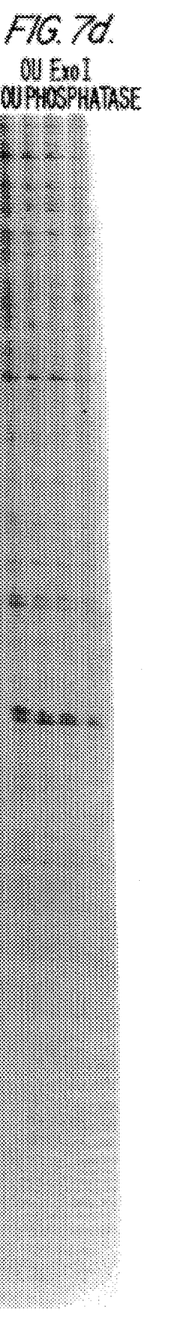

The enzymes were then heat-inactivated and the DNA diluted 20-fold. This was used as template (10 µl) using −40 primer and nucleotides as described above. Pre-treatment with both exonuclease and alkaline phosphatase yields the best sequence (FIG. 7C).

EXAMPLE 7

Cycle Sequencing with Fluorescein-labeled dUTP and Fluorescent Detection

In this example, the radioactive label is replaced by non-radioactive, fluorescein-labeled nucleotide (fluorescein-dUTP), Boeringer Mannheim Biochemicals). Cycle sequences were run using either single-stranded M13 DNA or double-stranded pUC18 plasmid DNA as template. The cycled labeling step was run using the universal (−40) sequencing primer in the presence of dATP, dGTP and fluorescein-dUTP. The reaction products were applied to a sequencing electrophoresis gel mounted in an ABI model 373A DNA sequencing instrument which detects sequencing products by fluorescence.

For the cycled labeling step, 0.05 pmole (or more) M13 DNA (0.125 µg) or 0.36 µg double-stranded plasmid DNA (pUC18), 2 µl ΔTaq Reaction Buffer (260 mM Tris-HCl (pH 9.5), 65 mM MgCl₂), 3 µl Fluorescein-dUTP Labeling Mix (10 µM fluorescein-dUTP, 1 µM dGTP, 1 µM dATP), 1 µl "−40" Primer (0.5 µM, 0.5 pmole/µl SEQ. ID. NO. 3: 5'-GTTTTCCCAGTCACGAC-3'), 2 µl ΔTaq DNA polymerase (8 U/µl) (in 10 mM Tris-HCl pH 8.0, 1 mM 2-mercaptoethanol, 0.5% TWEEN-20, 0.5% NP-40) and water were combined to a total volume of 18 µl in a 0.5 ml microcentrifuge vial, mixed well and overlaid with 15 µl light mineral oil. The vial was placed in the thermocycler (Perkin-Elmer Cetus Co.) and subjected to 30–50 cycles of 95° C. for 15 seconds and 60° C. for 30 seconds.

This combination of labeling reaction components allowed for the incorporation of a maximum of 3 fluorescein-dUTP molecules per annealed primer since dCTP was missing from the polymerization mixture as illustrated below:

Before Labeling Step
Primer
... GTTTTCCCAGTCACGAC SEQ ID NO: 3
... CAAAAGGGTCAGTGCTGCAACATTTTGCTG SEQ ID NO: 5
Template
After Labeling Step
Primer
... GTTTTCCCAGTCACGAC<u>GUUGUAAAA</u> SEQ ID NO: 6 (U= fluorescein dUMP)
... CAAAAGGGTCAGTGCTGCAACATTTTGCTG SEQ ID NO: 5
Template Following the labeling cycles, four vials were marked A, C, G, and T, and filled with 4 µl of the corresponding ΔTaq termination mix. Then the cycled labeling reaction was divided equally among the four termination vials (3.5 µl to each termination reaction vial), and overlaid with 15 µl of light mineral oil.

The four vials were placed in the thermocycler and 30–50 cycles performed from 95° C. for 30 seconds, 60° C. for 60 seconds, and 72° C. for 60 seconds. The reactions were stopped by adding 4 µl of Stop Solution (95% Formamide, 20 mM EDTA) to the termination reactions already under mineral oil. These samples were heated briefly at 75°–80° C. immediately prior to loading on a sequencing gel. Samples (5 µl) were loaded in four adjacent lanes (corresponding to one of the four termination reactions ddA, ddC, dG, and ddT) on a 6% acrylamide, 7M urea sequencing gel. Electrophoresis of sequencing reaction products was conducted using the Applied Biosystems 373A DNA Sequencing instrument overnight for 16 hours at 35 watts constant power. A high sensitivity fluorescence detector positioned near the bottom of the gel detects the fluorescent bands of DNA as they pass by during electrophoresis. The fluorescence intensity from each lane was collected using the accompanying ABI computer software using the filter channel optimal for fluorescein detection. This software was also used to normalize the data, subtracting baseline drift.

Figure 8A:
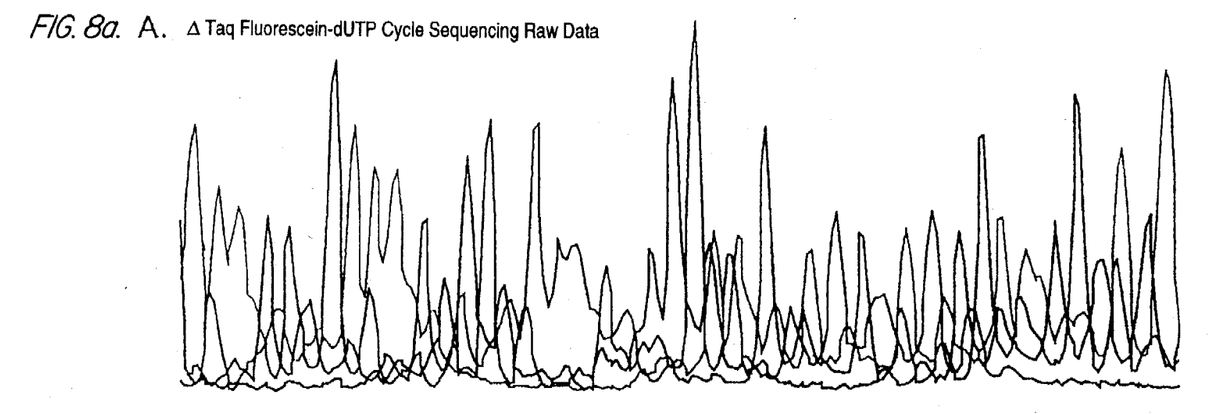
FIG. 8 is a graph of data from an Applied Biosystems instrument showing results of a sequencing experiment.
Figure 8B:
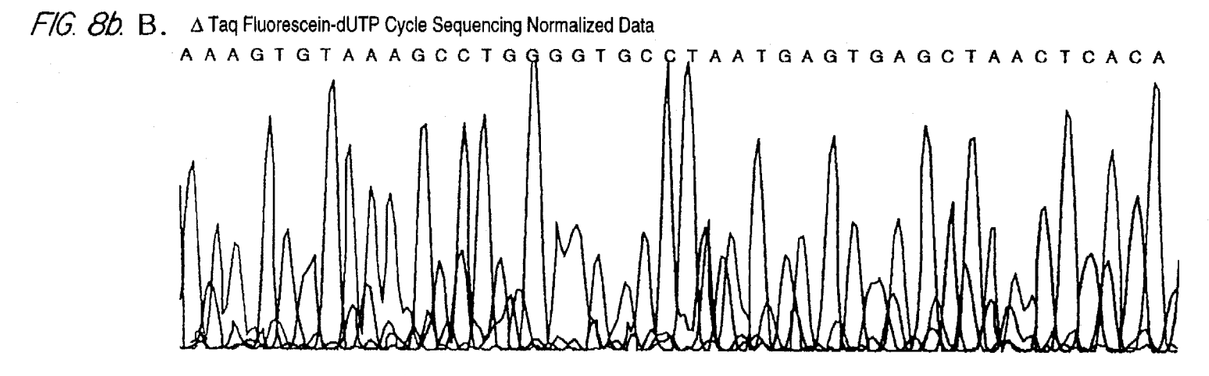

FIG. 8 shows the results of sequencing M13mp18 DNA, displaying the results covering the region from 175–217 bases from the 5' end of the primer. In panel A, the raw data from four adjacent lanes is displayed. These are colored as follows: Black, ddG reaction; Blue, ddC reaction; Green, ddA reaction; and Red, ddT reaction. The lower panel B shows the same results after software analysis which removes background drift and normalizes the average peak heights. The known sequence of the template DNA in this region is displayed above the peaks. Manual comparison of the graph and the sequence indicates that the method correctly displayed the sequence of all but one or two of the bases in this region.

EXAMPLE 8

Sequencing Asymmetric PCR Products by Pre-treatment with Alkaline Phosphatase Normally, the polymerase chain reaction (PCR) is performed with equal concentrations of two primers, leading to the geometric amplification of the sequence between their annealing sites. In principle, each cycle can double the amount of product DNA in the reaction mixture. The products of such "symmetric" PCR reactions are linear, double-stranded DNA molecules. Sometimes primers are added to the amplification reaction at unequal concentrations, with a concentration ratio of 10:1 to 500:1. Such "asymmetric" PCR reactions perform normally during the first several cycles, generating a geometrically increasing amount of double-stranded product DNA. Eventually, the supply of the lower-concentration primer is exhausted. From this point, further amplification cycles have only a single primer available, so they produce only one strand of product DNA. The concentration of this single-stranded product increases linearly with additional cycles. Thus the reaction products consist of a relatively small amount of double-stranded linear DNA and a larger concentration of single-stranded linear DNA. This single-stranded DNA can be used as template for DNA sequencing.

Gyllensten and Erlich, 85 *Proc. Natl. Acad. Sci. USA* 7652 (1988), describe a procedure for sequencing the single-stranded products of asymmetric PCR. The procedure requires the use of an ultrafilter in a centrifuge followed by drying of the concentrated DNA. This procedure takes several hours to complete and the use of the filter makes it expensive. Others (Brow, p. 189 in "PCR Protocols: A Guide to Methods and Applications", Academic Press, 1990) have described the use of alcohol precipitation to purify the DNA prior to sequencing. Again, this procedure takes several hours to complete. They suggest an alternative which requires no DNA purification but which requires the use of labeled primer and reduced concentrations of dNTPs in the PCR process Labeling the primer is an additional, time-consuming and expensive step, especially if only a few sequences are being performed.

The purification, or other steps, is required because the dNTPs used for the PCR interfere with the sequencing process. Applicant has discovered that these dNTPs can be removed much more rapidly, simply and inexpensively by the addition of a small amount of heat-labile alkaline phosphatase. Preferred alkaline phosphatases include the Shrimp Alkaline Phosphatase (United States Biochemical Corporation) and Calf-Intestine alkaline phosphatase which are sensitive to heating of 60°–70° C.

The PCR was performed in 100 μl volume using 50 pmol of one primer and 1 pmol of the second primer (50:1 primer ratio) in the buffer supplied in the GeneAmp kit (Perkin Elmer Cetus Corp.) with 2.5 units of AmpliTaq Taq DNA polymerase. The dNTPs were added to a concentration of 0.2 mM. Template was supplied by a single M13 plaque which contained an insert of approximately 1 Kb in size. The phage was eluted from the plaque in 100 μl of 10 mM Tris-HCl pH7.5, 1 mM EDTA and 5 μl used in the PCR. The vial was placed in the thermocycler and subjected to 50 cycles of 95° C., 1 minute; 55° C., 1 minute; and 72° C., 2 minutes.

Following amplification, an aliquot (10 μl) was removed and 2 units of alkaline phosphatase were added. This mixture was incubated at 37° C. for 10 minutes and then the phosphatase inactivated by incubation at 70° C. for 10 minutes.

Following this treatment, an aliquot of 7 μl was removed and sequenced using the normal procedures for the Sequenase Version 2.0 DNA sequencing kit (United States Biochemical Corporation). Sequences were of excellent quality with the alkaline phosphatase pre-treatment but unusable without alkaline phosphatase. This method is completed quickly, requiring only simple pipetting steps which can be readily performed by automated robots. The reagents are readily available and inexpensive. Similar, high-quality sequences have been obtained using amplified human genomic DNA with several primers.

---

Other embodiments are within the following claims:

1. A method for sequencing DNA, comprising the steps of:
    a) contacting a polynucleotide primer complementary to a region of said DNA to be sequenced, and said DNA to be sequenced, together in the presence of a DNA polymerase, and between one and three dNTPs at least one dNTP being labeled to allow extension of said primer by addition of one or more said dNTPs to said primer, to form an extended primer,
    b) dissociating said extended primer from said DNA,
    c) repeating steps a) and b) a plurality of times, and
    d) contacting said extended primer with said DNA to be sequenced in the presence of a DNA polymerase, four dNTPs and a chain terminating agent.

2. The method of claim 1, wherein said polymerase is Taq DNA polymerase.

3. The method of claim 2, wherein said polymerase is ΔTaq DNA polymerase.

4. The method of claim 1, wherein said polymerase is chosen from T7 DNA polymerase having a low exonuclease activity, Klenow, AMV reverse transcriptase, Bst DNA polymerase, Tth DNA pollEnerase, Vent polymerase, exo-free vent polymerase, and exo-free Klenow.

5. The method of claim 1, wherein said label is $^{35}$S.

6. The method of claim 1, wherein said label is a fluorescent label.

7. The method of claim 1, wherein said label is a chemiluminescent label.

8. The method of claim 1, wherein said label is a ligand detectable by indirect enzyme-linked assay.

9. The method of claim 1, wherein said plurality is between 10 to 200.

10. The method of claim 1, wherein said method further comprises after step d) a further step e) of separating said further extended primer from said DNA.

11. The method of claim 10, wherein said steps d) and e) are repeated a plurality of times.

12. The method of claim 11, wherein said plurality is between 10 to 200.

13. The method of claim 1, wherein said DNA is M13 DNA.

14. The method of claim 1, wherein said DNA is plasmid DNA.

15. The method of claim 1, wherein said DNA comprises an f1 origin.

16. The method of claim 1, wherein said DNA is lambda DNA.

17. The method of claim 1, wherein said DNA is produced by amplification.

18. The method of claim 17, wherein said amplification is by PCR.

* * * * *